United States Patent [19]
Corey et al.

[11] Patent Number: 5,885,595
[45] Date of Patent: Mar. 23, 1999

[54] COSMETIC COMPOSITION WITH A RETINOL FATTY ACID ESTER

[75] Inventors: Joseph Corey, Waterbury; Peter Ladislav Dorogi, Norwalk; Alan Joel Meyers, Trumbull; Anthony Vargas, Monroe, all of Conn.

[73] Assignee: Elizabeth Arden Co., Division of Conopco, Inc., New York, N.Y.

[21] Appl. No.: 834,885

[22] Filed: Apr. 7, 1997

Related U.S. Application Data

[60] Provisional application No. 60/017,559, May 13, 1996, and provisional application No. 60/025,803, Aug. 28, 1996.

[51] Int. Cl.$^6$ .............................. A61K 7/00; A61K 31/07
[52] U.S. Cl. ..................... 424/401; 514/725; 514/844; 514/864; 514/859; 514/887
[58] Field of Search .............. 424/401; 514/844, 514/725, 887, 859, 864

[56] References Cited

U.S. PATENT DOCUMENTS

| | | | |
|---|---|---|---|
| 4,603,146 | 7/1986 | Kligman | 514/559 |
| 4,877,805 | 10/1989 | Kligman | 514/381 |
| 4,887,805 | 12/1989 | Herbert et al. | 271/94 |
| 5,244,665 | 9/1993 | Natraj et al. | 424/401 |
| 5,476,661 | 12/1995 | Pillai et al. | 424/401 |
| 5,536,740 | 7/1996 | Granger et al. | 514/392 |
| 5,665,367 | 9/1997 | Burger et al. | 424/401 |
| 5,705,144 | 1/1998 | Harding et al. | 424/59 |

FOREIGN PATENT DOCUMENTS

| | | |
|---|---|---|
| 0 512 814 | 11/1992 | European Pat. Off. . |
| 0 710 478 | 10/1994 | European Pat. Off. . |
| 0 631 772 | 1/1995 | European Pat. Off. . |
| 94/07462 | 4/1994 | WIPO . |
| 94/09756 | 5/1994 | WIPO . |

OTHER PUBLICATIONS

Chem. Abs. 120:330825s, 1994.
Chem. Abs. 120:330820m, 1994.
"Vitamins and the Skin", Cosmetics and Toiletries, vol. 108, Dec. 1993, pp. 79–94.
"Rapid Synthesis and Purification of Vitamin A Esters" Nutrition and Food Safety Laboratory, I.N.R.A.C.R.J., 78352 Josas, France, pp. 1272–1273, Dec. 1992.
"Application of Retinol to Human Skin in Vivo Induces Epidermal Hyperplasia and Cellular Retinoid Binding Proteins Characteristic of Retinoic Acid but Without Measurable Retinoic Acid Levels or Irritation", The Society for Investigative Dermatology, Inc., 1995, pp. 549–556.

*Primary Examiner*—Thurman K. Page
*Assistant Examiner*—James M. Spear
*Attorney, Agent, or Firm*—Milton L. Honig

[57] ABSTRACT

A method and composition is provided for enhancing skin radiance and treating chronoaging conditions including wrinkles and dermatological disorders including acne, follicular and lesional papules, actinic keratoses, oily skin and rosacea comprising: (i) a safe and effective amount of an unsaturated $C_{18}$–$C_{30}$ fatty acid ester of retinol; and (ii) a safe and effective amount of a cosmetically acceptable carrier, the composition being stable for at least four weeks at 43° C. An unsaturated $C_{18}$–$C_{30}$ fatty acid ester of retinol is the active component which is applied to the skin in a cosmetically acceptable carrier. The most preferred unsaturated retinol fatty acid ester is retinyl linoleate. The composition is stable and remains active for at least four weeks at 43° C.

2 Claims, No Drawings

5,885,595

COSMETIC COMPOSITION WITH A RETINOL FATTY ACID ESTER

This application claims the benefits of U.S. Provisional Applications Nos. 60/017,559 filed May 13, 1996, and 60/025,803 filed Aug. 28, 1996.

BACKGROUND OF THE INVENTION

1. Field of the Invention

The present invention concerns a cosmetic composition containing specific long chain unsaturated retinol fatty acid esters useful for skin care treatment for chronoaging conditions and dermatologic disorders to provide skin radiance without substantial irritation.

2. The Related Art

Skin is subject to deterioration through dermatologic disorders and normal aging (chronoaging) as well as extrinsic factors (environmental). Dermatologic disorders, other than chronoaging include acne, follicular and lesional papules, actinic keratoses, oily skin and rosacea.

Chronoaging results in the thinning and general degradation of skin. As skin naturally ages, there is reduction in the cells and blood vessels that supply the skin. There is also a flattening of the dermal-epidermal junction which results in weaker mechanical resistance. Aging individuals increasingly develop facial fine lines, wrinkles, leatheriness, yellowing or sallowness, sagging, mottling (hyperpigmentation), age spots and the general signs of aging.

Extrinsic factors are primarily those caused by exposure to sun. Changes are most prominent in light skinned individuals who burn easily and tan poorly. The results of photo damage may be identical to those of aging except may appear at an accelerated rate. Wrinkling, yellowing, leatheriness, mottling and hyperpigmentation are all associated with sun damage. Most disturbing to many individuals is the wrinkling effect. As a result, there have been many articles reporting cosmetic treatments aimed at the elimination of wrinkles.

Skin care compositions containing retinoids have become quite prominent in recent years. Retinoic acid, also known as Vitamin A acid or Tretinoin, is well known for treatment of acne. Even more recently, the retinoids have been suggested as treatment against photoaging and sun damage. For instance, U.S. Pat. No. 4,603,146 discloses Vitamin A acid in an emollient vehicle to prevent skin aging. U.S. Pat. No. 4,877,805 suggests a number of retinoids as useful for restoring and reversing sun damage in human skin. EP 0 631 772 describes use of retinol in combination with an irritation ameliorating amount of glycolic acid.

Recent clinical investigations of the responses of normal skin to retinol as compared to retinoic acid indicate that retinoic acid rather than retinol irritates skin and is the erythemogenic agent. Kang et al, "Application of Retinol to Human Skin In Vivo ("Induces Epidermal Hyperplasia and Cellular Retinoid Binding Proteins Characteristic of Retinoic Acid but Without Measurable Retinoic Acid Levels or Irritation" Journal of Investigative Dermatology #4, (Oct. 95), pp. 549–555. It appears that a cellular retinol binding protein (CRBP) in the epidermis converts retinol to its retinol esters by inhibiting the synthesis of retinol to retinoic acid. Supra. The regulation of retinoic acid concentrations to control skin irritation is lost when a consumer just applies retinol to the skin.

Retinols, as well as, retinol (vitamin A) and many of its esters, are known in the art to require formulation with stabilizing systems to provide products which do not lose activity in storage. See Chem. Abs., 120: 330825s describing U.S. Ser. No. 926,606 filed Aug. 6, 1992 now abandoned by Johnson & Johnson Consumer Products, Inc.; Chem Abs. 120: 330820m describing JP 06 32774 owned by Shiseido Co. Ltd.

Short chain retinol derivatives, such as retinyl acetate and retinyl propionate, are known to lose activity in storage. Retinyl palmitate having a $C_{16}$ chain is also known as the most stable of the available vitamin A esters. (See ldson, B. "Vitamins and the Skin", *Cosmetics & Toiletries*, Vol. 108, December 1993, p. 79, 86.

It has now been discovered that skin fatty acid esters of retinol which are both unsaturated and long chain ($C_{18}$–$C_{30}$) may be formulated without requiring a stabilizing system to retain their activity during storage. This discovery is particularly surprising because it appears to go against conventional teachings, that saturated, and not saturated bonds are more stable since compounds containing saturated bonds would be expected to retain their activity longer than compounds containing unsaturated bonds.

These esters have also been observed to enhance overall skin radiance and treat dermatological and chronoaging conditions without skin irritation.

Another object of the present invention is to provide a skin composition which treats dermatological disorders (such as acne, follicular and lesional papules, actinic keratoses, oily skin and rosacea) and chronoaging conditions (including wrinkling and fine lines, leatheriness, yellowing, sagging, sallowness, mottling (hyperpigmentation), age spots and general aging signs) at least or more effectively than retinol and its esters which are saturated.

These and other objects of the present invention will become more readily apparent from the following summary and detailed discussion.

SUMMARY OF THE INVENTION

A cosmetic composition which is useful for enhancing skin radiance without substantial irritation is provided which includes a safe and effective amount of a $C_{18}$–$C_{30}$ unsaturated fatty acid ester of retinol and a safe and effective amount of a cosmetically acceptable carrier. A method of enhancing skin radiance and treating chronoaging conditions with the composition is also described.

DETAILED DESCRIPTION OF THE INVENTION

The active essential for the compositions and methods of using the formulas of the present invention is a $C_{18\text{-}30}$ fatty acid ester of retinol which is unsaturated. Retinyl palmitate, retinyl acetate, retinyl propionate and retinol itself are not stable and thus lose activity in the inventive formulas. Thus retinol ester derivatives which are saturated also fall outside the scope of this invention.

Retinol esters which are effective include retinyl linoleate, retinyl linoleneate, retinyl oleate, retinyl arachidonate, and isomers and mixtures thereof. Most preferred is retinyl linoleate.

"Safe and effective amounts" of the $C_{18}$–$C_{30}$ unsaturated esters are to be used within cosmetic compositions of the present invention. The term "safe and effective amounts" is defined as any amount sufficient to significantly induce a positive thickening of the skin epidermis to be treated, but low enough to avoid serious side effects (at a reasonable benefit/risk ratio), within the scope of sound medical judgement. The safe and effective amount of the esters will vary with the age and physical condition of the consumer, the condition of the skin, the duration of the treatment, the nature of any concurrent treatment the specific ester employed, the particular cosmetically-acceptable carrier utilized, and like factors in the knowledge and expertise of any attending physician. Generally the amounts of the unsaturated esters may range from 0.0001% to 10%, preferably from 0.1 to 5%, more preferably from 0.2 to 0.5% by weight.

Besides the unsaturated esters of the invention, compositions of the present invention will utilize a cosmetically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 25 to 40% by weight.

Emollient materials may also serve as cosmetically acceptable carriers. These may be in the form of silicone oils and synthetic esters. Amounts of the emollients may range anywhere from 0.1 to 50%, preferably between 1 and 45% by weight, optimally between 10 and 40 wt. %.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters and squalane are satisfactory polyhydric alcohol esters. Also useful are $C_{11}$–$C_{30}$ nonring ester derivatives of salicylic acid such as tridecyl salicylate.

(4) Wax esters such as beeswax, spermaceti, myristyl myristate, stearyl stearate.

(5) Sterols esters, of which cholesterol fatty acid esters are examples thereof.

The most preferred esters are $C_{11}$–$C_{30}$ nonring ester derivatives of salicylic acid such as tridecylsalicylate.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably butylene glycol. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides, cellulosic derivatives and natural gums. Among useful cellulosic derivatives are sodium carboxymethylcellulose, hydroxypropyl methylcellulose, polyacrylamide hydroxypropyl cellulose, hydroxyethyl cellulose, ethyl cellulose and hydroxymethyl cellulose. Natural gums suitable for the present invention include guar, xanthan, sclerotium, carrageenum, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Cosmetic compositions of the present invention may be in any form. These forms may include lotions, creams, roll-on formulations, mousses, aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_2$, Vitamin $B_6$, Vitamin C and Biotin. One source for Vitamin C is a product sold under the trademark of Vitazyme available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2$–$C_{25}$ α-hydroxy alkanoic acids may also be incorporated into compositions of this invention. Illustrative of this group of materials are glycolic, lactic, α-hydroxyoctanoic acids, esters and salts thereof. The salts may be selected from alkalimetal, ammonium and $C_1$–$C_{20}$ alkyl or alkanolammonium counterions. Levels of α-hydroxyalkanoic acids may range from 0.001 to 10%, preferably between 0.2 and 1%, optimally between 0.4 and 0.5% by weight. A beta hydroxy alkanoic acid which may be used includes salicylic acid.

Another adjunct ingredient can be that of an enzyme. Particularly preferred is superoxide dismutase, commercially available as Biocell SOD from the Brooks Company, USA.

Ceramide compounds may also be included in the compositions, such as those described in U.S. Pat. No. 5,476,661 owned by Elizabeth Arden, herein incorporated by reference.

Natural vegetable materials from renewable resources are often desirable in cosmetic compositions. For instance, cosmetic compositions of the present invention may include β-glucan derived from oats.

Colorants, fragrances, opacifiers and abrasives may also be included in compositions of the present invention. Each of these substances may range from about 0.05 to about 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

A skin cream formulation of the oil in water type according to the present invention is described in Table I.

TABLE I

| CHEMICAL | % W/W |
|---|---|
| Water | qs |
| Disodium EDTA | 0.10 |
| Polysorbate 40 | 1.00 |
| Propylene Glycol | 3.00 |
| Methylparaben | 0.25 |
| Retinyl linoleate | 0.30 |
| Isopropyl Palmitate | 5.00 |
| Isostearyl Isostearate | 3.00 |
| Silicone 200/100 Fluid (Dimethicone) | 5.00 |
| Silicone 344 Fluid (Cyclomethicone) | 15.00 |
| Imidazolidinyl Urea | 0.20 |
| Sepigel 305 (Laureth-7, Polyacrylamide, Isoparaffin) | 3.00 |

EXAMPLE 2

Another skin cream formulation of the oil in water type according to the present invention is described in Table II.

TABLE II

| CHEMICAL | % W/W |
|---|---|
| Water | qs |
| Disodium EDTA | 0.10 |
| Butylene Glycol | 3.00 |
| Glycerin | 3.00 |
| Methylparaben | 0.25 |
| Retinyl Linoleate | 0.30 |
| Squalane | 1.00 |
| Shea Butter | 0.50 |
| Cetyl Alcohol | 1.50 |
| Octyl Palmitate | 2.00 |
| Tridecyl Salicylate | 5.00 |
| Octyl Stearate | 2.00 |
| Silicone 344 Fluid (Cyclomethicone) | 2.00 |
| Imidazolidinyl Urea | 0.20 |
| Sepigel 305 (Laureth-7, Polyacrylamide, Isoparaffin) | 3.50 |

EXAMPLE 3

Still another skin cream formulation of the oil in water type according to the present invention is described in Table III.

TABLE III

| CHEMICAL | % W/W |
|---|---|
| Water | qs |
| Disodium EDTA | 0.10 |
| Butylene Glycol | 2.00 |
| Glycerin | 3.00 |

TABLE III-continued

| CHEMICAL | % W/W |
| --- | --- |
| Methylparaben | 0.25 |
| Retinyl linoleate | 0.30 |
| Shea Butter | 0.50 |
| Cetyl Alcohol | 1.00 |
| PEG-100 Glycerol Monostearate | 4.00 |
| Tridecyl Salicylate | 5.00 |
| Tocopheryl Linoleate | 0.50 |
| Silicone 200 Fluid (Dimethicone) | 2.00 |
| Imidazolidinyl Urea | 0.20 |

EXAMPLE 4

A microemulsion formulation according to the present invention is described in Table IV.

TABLE IV

| CHEMICAL | % W/W |
| --- | --- |
| PPG-5-Ceteth-20 | 4.00 |
| PEG-40 Hydrogenated Castor Oil | 1.75 |
| Polyglyceryl-10 Decaoleate | 10.00 |
| PEG-8 Caprylic/Capric Glycerides | 10.00 |
| SDA Alcohol 40B | 12.00 |
| Isodecyl Neopentanoate | 16.00 |
| Glyceryl Triocatanoate | 8.00 |
| Cyclomethicone (DC 344 Fluid) | 8.00 |
| Propylparaben | 0.10 |
| Isostearic Acid | 2.50 |
| Retinyl Behenate | 0.30 |
| Phenoxyethanol | 0.30 |
| Deionized Water | qs |

EXAMPLE 5

A skin cream formulation of the water in oil type according to the present invention is described in Table V.

TABLE V

| CHEMICAL | % W/W |
| --- | --- |
| Cyclomethicone (DC 344 Fluid) | 12.00 |
| Dimethicone (DC 200/10 fluid) | 2.00 |
| Dimethicone Copolyol | 2.50 |
| Cetyl Dimethicone | 0.50 |
| C12–15 Alkyl Benzoate | 3.00 |
| Retinyl Linoleate | 0.10 |
| Glycerin | 3.00 |
| Propylene Glycol | 2.00 |
| Disodium EDTA | 0.10 |
| Methylparaben | 0.25 |
| Sodium Chloride | 1.20 |
| Phenoxyethanol | 0.20 |
| Deionized Water | qs |

EXAMPLE 6

An anhydrous serum formulation according to the present invention is described in Table VI.

TABLE VI

| CHEMICAL | % W/W |
| --- | --- |
| Sepigel 305 | 1.50 |
| SD Alcohol 40 B (200 proof) | 20.00 |
| Cyclomethicone (DC 344 Fluid) | 2.50 |

TABLE VI-continued

| CHEMICAL | % W/W |
| --- | --- |
| Squalene | 1.00 |
| Octyl Isononanoate | 2.50 |
| Dimethicone (DC 200 Fluid | 5.20 |
| Isononyl Isononanoate | 30.00 |
| Butylene Glycol | 1.00 |
| Propylparaben | 0.10 |
| Retinyl linoleate | 0.50 |
| Dimethiconol | 2.75 |

EXAMPLE 7

A sunscreen lotion formulation of the oil in water type according to the present invention is described in Table VII.

TABLE VII

| CHEMICAL | % W/W |
| --- | --- |
| Water | qs |
| Disodium EDTA | 0.10 |
| Butylene Glycol | 2.00 |
| Glycerin | 5.00 |
| Methylparaben | 0.25 |
| Retinyl Linoleneate | 0.10 |
| Octyl Methoxycinnamate | 7.50 |
| Benzophenone-3 | 2.50 |
| Shea Butter | 0.50 |
| Cetyl Alcohol | 1.50 |
| Octyl Palmitate | 2.00 |
| C12–15 Alkyl Bezoate | 2.00 |
| Silicone 200 Fluid (Dimethicone) | 1.00 |
| Imidazolidinyl Urea | 0.20 |
| Sepigel 305 (Laureth-7, Polyacrylamide, Isoparaffin) | 3.50 |

EXAMPLE 8

To determine the cumulative irritation potential of inventive composition potential of inventive composition versus compositions outside the scope of the invention six (6) skin cream samples were prepared according to Example 1 with various amounts of retinyl linoleate, retinyl acetate, and retinol as follows:

TABLE VIII

| SAMPLE | ACTIVE % W/W |
| --- | --- |
| Control | no active |
| A | 0.3% retinyl linoleate |
| B | 0.1% retinyl linoleate |
| C | 0.2% retinyl acetate |
| D | 0.1% retinyl acetate |
| E | 0.025% retinol and retinyl acetate and 0.1% retinyl linoleate |

The samples including the control samples were patched out on the upper backs of each of 29 panelists for 14 days. The test sites were evaluated for irritation by a trained grader. Each sample was given a Berger & Bowman score and ranked according to categories. Category I indicated mild material with no experimental irritation, Category II indicates probably mildness and Category III indicates possible mildness. The cumulative scores based on N=10 and categories for the samples are as follows:

TABLE IX

| SAMPLE | CUMULATIVE SCORE BASED ON N = 10 | CATEGORY |
|---|---|---|
| A Control | 250 | III |
| A | 100 | II |
| B | 86 | II |
| C | 214 | III |
| D | 147 | III |
| E | 192 | III |

It was thus observed that samples containing retinyl lineolate according to the invention were significantly less irritating than samples containing retinyl acetate either alone or in combination with retinyl linoleate and retinol.

EXAMPLE 9

The stability of the inventive composition containing (Retinyl linoleate was compared against stability values of compositions containing either retinol or retinyl acetate as follows:

Three base compositions containing 0.3 wt. % of retinol, retinyl acetate and retinyl linoleate, respectively, were prepared as described in Example 2. The samples were stored for at least four weeks at 60° C., 43° C. and 50° C. and at the end of each week the samples were analyzed to determine percent activity remaining for each active with the following results.

TABLE X

6° C. STORAGE

| ACTIVE | INITIAL | 2 WK | 4 WK |
|---|---|---|---|
| RETINOL | 100% | 88% | 93% |
| RETINYL ACETATE | 100% | 100% | 100% |
| RETINYL LINOLEATE | 100% | 100% | 100% |

TABLE XI

43° C. STORAGE

| ACTIVE | INITIAL | 2 WK. | 4WK. |
|---|---|---|---|
| RETINOL | 100% | 96% | 77% |
| RETINYL ACETATE | 100% | 89% | 79% |
| RETINYL LINOLEATE | 100% | 100% | 100% |

TABLE XII

50° C. STORAGE

| ACTIVE | INITIAL | 2 WK | 4 WK |
|---|---|---|---|
| RETINOL | 100% | 87% | 62% |
| RETINYL ACETATE | 100% | 81% | 65% |
| RETINYL LINOLEATE | 100% | 100% | 100% |

It was thus observed that retinyl linoleate retained 100% of its activity in formulation for at least four weeks even under extreme conditions, both retinol and retinyl acetate lost stability as much as 35% of its activity.

EXAMPLE 10

Three sample compositions having the following active ingredients were prepared: (1) 0.05% tretinoin (all trans retinoic acid), (2) 0.75% retinol and 8% L-lactic acid, and (3) 0.3% retinyl linoleate. The samples were provided to 200 volunteers having fine wrinkling, coarse wrinkling, discrete pigmentation, mottled pigmentation, laxity, sallowness, rough texture, clogged pores, overall photodamage, actinic keratoses, follicular papules, lesional papules, lesions-pustules, diffuse redness and overall rosacea. The volunteers topically applied the samples to their faces. Clinical photos were taken. Improvement of the above listed skin conditions was clinically discerned and graded over a six (6) month period (at 3, 8, 13, 16 and 24 weeks) with the following results.

Fine wrinkles were substantially improved after only eight (8) weeks of treatment with retinyl linoleate products and to the level of at least the retinol or retinoic acid containing samples Discrete and mottled pigmentation, rough texture and clogged pores was markedly improved after six (6) months and the inventive formulation was at least as effective as the comparative retinol or retinoic acid containing samples.

Clinical assessments of skin treated with the inventive formulation also showed improvements in overall photodamage to the same degree than improvements observed with skin treated with the retinol or retinoic acid containing samples at 16 weeks. At 24 weeks results of all samples were similar.

Actinic keratoses were assessed as zero for all samples after six (6) months as at baseline.

Papules, including both follicular and lesional papules, treated with the inventive formulation were markedly improved after six (6) months to the same degree as skin treated with the retinol or retinoic acid containing formulas.

Diffuse redness and overall rosacea were improved to a greater degree by the inventive formulation compared to the retinol or retinoic acid.

Subjects were asked to self assess their skin condition after treatment with the following results.

Overall clarity and brightness of the skin were assessed as substantially the same when the skin was treated with the inventive formula as opposed to the comparative samples.

Improvement in skin tone, uneven skin color, skin pores, pimples, dryness, skin texture, fine lines and overall radiance were rated as the same or better with the retinyl linoleate containing product versus the retinol or retinoic acid containing samples.

In summary, clinical test results of the inventive product in comparison to the retinol containing products indicated improvement to the same or better degree for a variety of dermatological and chronoaging skin conditions.

What is claimed is:

1. A cosmetic composition useful for enhancing skin radiance without substantial irritation and for treating chronoaging conditions including wrinkles and fine lines, leatheriness, yellowing, sagging, mottling (hyperpigmentation), and age spots and dermatological disorders including acne, follicular and lesional papules, actinic keratoses, oily skin and rosacea comprising:

(i) from 0.001 to about 0.3% of retinyl linoleate; and (ii) a safe and effective amount of a cosmetically acceptable carrier, the retinyl linoleate being stable in the carrier for at least four weeks at 43° C.

2. A method for increasing skin radiance without substantial irritation and for treating chronaging conditions including wrinkles and fine lines, leatheriness, yellowing, sagging, mottling (hyperpigmentation), and age spots and dermatological disorder including acne, follicular and lesional papules, actinic keratoses, oily skin and rosacea, the method comprising applying to the skin a cosmetic composition comprising:

(i) from 0.001 to about 0.3% of retinyl linoleate, and (ii) a safe and effective amount of a cosmetically acceptable carrier, the retinyl linoleate being stable in the carrier for at least four weeks at 43° C.

* * * * *